(12) United States Patent
Tan et al.

(10) Patent No.: US 8,927,609 B2
(45) Date of Patent: Jan. 6, 2015

(54) CO-ATTRITED STABILIZER COMPOSITION

(71) Applicant: FMC Corporation, Philadelphia, PA (US)

(72) Inventors: Zheng Tan, Princeton, NJ (US); Aaron Chip Venables, Yardley, PA (US); Michael Sestrick, Yardley, PA (US); Nadia Yaranossian, Brussels (BE); Jeremy Ondov, New York, NY (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 13/690,395

(22) Filed: Nov. 30, 2012

(65) Prior Publication Data

US 2013/0150462 A1 Jun. 13, 2013

Related U.S. Application Data

(60) Provisional application No. 61/568,672, filed on Dec. 9, 2011.

(51) Int. Cl.
*A61K 47/00* (2006.01)
*C08L 1/04* (2006.01)
*A23C 9/154* (2006.01)
*A23L 1/0534* (2006.01)
*C08L 1/28* (2006.01)
*A23C 11/10* (2006.01)
*A23L 2/52* (2006.01)
*A23L 2/66* (2006.01)

(52) U.S. Cl.
CPC .............. *C08L 1/04* (2013.01); *A23L 1/0534* (2013.01); *C08L 1/286* (2013.01); *A23C 11/103* (2013.01); *A23L 2/52* (2013.01); *A23C 9/1544* (2013.01); *C08L 2205/02* (2013.01); *A23L 2/66* (2013.01)
USPC ............ 514/781; 426/654; 426/590; 426/598

(58) Field of Classification Search
USPC ........................................................ 424/400
See application file for complete search history.

(56) References Cited

U.S. PATENT DOCUMENTS

| | | | |
|---|---|---|---|
| 2,978,446 A | 4/1961 | Battista et al. | |
| 3,023,104 A | 2/1962 | Battista et al. | |
| 3,145,146 A | 8/1964 | Lieberman et al. | |
| 3,146,168 A | 8/1964 | Battista et al. | |
| 3,539,365 A * | 11/1970 | Durand et al. | 106/162.8 |
| 3,573,058 A | 3/1971 | Tiemstra | |
| 3,639,169 A | 2/1972 | Broeg et al. | |
| 4,017,598 A | 4/1977 | Ohno et al. | |
| 4,110,476 A | 8/1978 | Rhodes | |
| 4,263,334 A | 4/1981 | McGinley | |
| 4,264,637 A | 4/1981 | Braverman | |
| 4,426,518 A | 1/1984 | Omiya | |
| 4,693,750 A | 9/1987 | Bauer et al. | |
| 4,744,987 A | 5/1988 | Mehra et al. | |
| 4,980,193 A | 12/1990 | Tuason, Jr. et al. | |
| 5,082,684 A | 1/1992 | Fung | |
| 5,192,569 A | 3/1993 | McGinley et al. | |
| 5,272,137 A | 12/1993 | Blase et al. | |
| 5,286,510 A | 2/1994 | Bauer et al. | |
| 5,366,724 A | 11/1994 | St. Pierre et al. | |
| 5,366,742 A | 11/1994 | Tuason, Jr. et al. | |
| 5,409,907 A | 4/1995 | Blase et al. | |
| 5,415,804 A | 5/1995 | Minami et al. | |
| 5,505,982 A | 4/1996 | Krawczyk et al. | |
| 5,543,511 A | 8/1996 | Bergfeld et al. | |
| 5,573,777 A | 11/1996 | Serpelloni et al. | |
| 5,605,712 A | 2/1997 | Bertrand et al. | |
| 5,607,716 A | 3/1997 | Doherty et al. | |
| 5,609,898 A | 3/1997 | Kaji et al. | |
| 5,709,896 A | 1/1998 | Hartigan et al. | |
| 5,725,886 A | 3/1998 | Erkoboni et al. | |
| 5,747,067 A | 5/1998 | Auguello et al. | |
| 5,769,934 A | 6/1998 | Ha et al. | |
| 5,789,004 A | 8/1998 | Hogan et al. | |
| 5,866,166 A | 2/1999 | Staniforth et al. | |
| 6,010,734 A | 1/2000 | Whelan et al. | |
| 6,025,007 A | 2/2000 | Krawczyk | |
| 6,037,380 A * | 3/2000 | Venables et al. | 514/781 |
| 6,079,630 A | 6/2000 | Schroeder | |
| 6,106,865 A | 8/2000 | Staniforth et al. | |
| 6,117,474 A | 9/2000 | Kamada et al. | |

(Continued)

FOREIGN PATENT DOCUMENTS

| | | |
|---|---|---|
| EP | 1226818 A1 | 7/2002 |
| EP | 1 681 048 A1 | 7/2006 |

(Continued)

OTHER PUBLICATIONS

Bowman, B.J. Ofner, C.M.; Schott, H. "Colloidal Dispersions" Chapter 21 of Remington: The Science and Practice of Pharmacy. 21$^{st}$ Edition. 2005. Lippincott Williams and Wilkins. Philadelphia, PA.*

Sigma product info of carboxymethylcellulose, sodium salt (published Aug. 2003).*

Bowman, B.J. Ofner, C.M.; Schott, H. "Colloidal Dispersions" Chapter 21 of Remington: The Science and Practice of Pharmacy. 21st Edition. 2005. Lippincott Williams and Wilkins. Philadelphia, PA.*

Mitchell, S.A., et al., 'A Compaction Process to enhance dissolution of poorly water-soluble drugs using hydroxypropyl methylcellulose'. International Journal of Pharmaceutics, 250, pp. 3-11, 2003.

(Continued)

*Primary Examiner* — Sean Basquill
*Assistant Examiner* — Andrew S Rosenthal
(74) *Attorney, Agent, or Firm* — FMC Corporation

(57) ABSTRACT

The present invention is directed to a co-attrited stabilizer composition comprising: (i) microcrystalline cellulose and (ii) carboxymethyl cellulose, wherein the carboxymethyl cellulose has a degree of substitution of from 0.95-1.5 and a viscosity of less than 100 cps. The composition is useful as a stabilizer, particularly, in food and pharmaceutical applications.

16 Claims, No Drawings

(56) References Cited

U.S. PATENT DOCUMENTS

| | | | |
|---|---|---|---|
| 6,228,213 B1 | 5/2001 | Hanna et al. | |
| 6,235,947 B1 | 5/2001 | Yoshinari et al. | |
| 6,264,981 B1 | 7/2001 | Zhang et al. | |
| 6,270,830 B1 | 8/2001 | Kamada et al. | |
| 6,368,649 B1 | 4/2002 | van Bommel | |
| 6,372,782 B1 * | 4/2002 | Patel et al. | 514/456 |
| 6,391,368 B1 | 5/2002 | Tuason et al. | |
| 6,432,448 B1 | 8/2002 | Augello et al. | |
| 6,440,474 B1 | 8/2002 | Buliga et al. | |
| 6,475,539 B1 | 11/2002 | Dewille et al. | |
| 6,500,462 B1 | 12/2002 | Augello et al. | |
| 6,503,918 B2 | 1/2003 | Yoshinari et al. | |
| 6,517,871 B1 | 2/2003 | Venkatesh et al. | |
| 6,548,093 B1 | 4/2003 | Collinge et al. | |
| 6,689,405 B1 | 2/2004 | Tuason, Jr. et al. | |
| 6,709,713 B2 | 3/2004 | Augello et al. | |
| 6,723,342 B1 | 4/2004 | Augello et al. | |
| 6,726,949 B2 | 4/2004 | Adolphi et al. | |
| 6,752,939 B2 | 6/2004 | Gereg | |
| 6,753,017 B2 | 6/2004 | Berkulin et al. | |
| 6,936,277 B2 | 8/2005 | Staniforth et al. | |
| 6,936,628 B2 | 8/2005 | Lee | |
| 7,462,232 B2 | 12/2008 | Tuason et al. | |
| 7,625,622 B2 | 12/2009 | Teckoe et al. | |
| 7,785,089 B2 | 8/2010 | Teckoe et al. | |
| 7,879,382 B2 | 2/2011 | Tuason et al. | |
| 2003/0017204 A1 | 1/2003 | Augello et al. | |
| 2003/0129238 A1 | 7/2003 | Augello et al. | |
| 2004/0071821 A1 | 4/2004 | Ashourian et al. | |
| 2004/0121006 A1 | 6/2004 | Narita et al. | |
| 2004/0137043 A1 | 7/2004 | Augello et al. | |
| 2004/0185161 A1 | 9/2004 | Ashourian et al. | |
| 2004/0258827 A1 | 12/2004 | Shen et al. | |
| 2005/0147710 A1 | 7/2005 | Teckoe et al. | |
| 2005/0220824 A1 | 10/2005 | Kessel et al. | |
| 2005/0233046 A1 | 10/2005 | Krawczyk et al. | |
| 2005/0233053 A1 | 10/2005 | Shen et al. | |
| 2005/0266116 A1 | 12/2005 | Teckoe et al. | |
| 2006/0127451 A1 | 6/2006 | Augello et al. | |
| 2008/0131505 A1 | 6/2008 | Li et al. | |
| 2008/0131543 A1 | 6/2008 | Teckoe et al. | |
| 2008/0213360 A1 | 9/2008 | Thoorens et al. | |
| 2009/0110799 A1 | 4/2009 | Funami et al. | |
| 2009/0130287 A1 | 5/2009 | Tuason et al. | |
| 2011/0151097 A1 | 6/2011 | Tuason et al. | |
| 2013/0064953 A1 * | 3/2013 | Bache et al. | 426/573 |

FOREIGN PATENT DOCUMENTS

| | | |
|---|---|---|
| GB | 1010477 | 11/1965 |
| GB | 1 567 049 | 5/1980 |
| GB | 2395413 A | 5/2004 |
| JP | 08-151481 A | 6/1996 |
| JP | 9266779 | 10/1997 |
| JP | 10-056960 | 3/1998 |
| JP | 10-237220 A | 9/1998 |
| JP | 11-046723 A | 2/1999 |
| JP | 11-299435 A | 11/1999 |
| JP | 2000-184853 | 7/2000 |
| JP | 2001-190220 A | 7/2001 |
| JP | 2002-125587 A | 5/2002 |
| JP | 2002345401 A2 | 12/2002 |
| JP | 2005-245217 | 9/2005 |
| WO | WO 81-02521 A1 | 9/1981 |
| WO | WO 94/24888 A1 | 11/1994 |
| WO | WO 9502966 * | 2/1995 |
| WO | WO 98/56826 A1 | 12/1998 |
| WO | WO 00/04862 A2 | 2/2000 |
| WO | WO 01/19348 A1 | 3/2001 |
| WO | WO 0132150 | 5/2001 |
| WO | WO 0132152 | 5/2001 |
| WO | WO 02/49451 A2 | 6/2002 |
| WO | WO 03/003843 A1 | 1/2003 |
| WO | WO 03/090558 A1 | 11/2003 |
| WO | WO 03/096976 A2 | 11/2003 |
| WO | WO 2005/030177 A2 | 4/2005 |
| WO | WO 2005/096832 A2 | 10/2005 |
| WO | WO 2006/131963 A1 | 12/2006 |
| WO | WO 2010136157 A1 * | 12/2010 |

OTHER PUBLICATIONS

Kleinebudde, P., 'Roll Compaction/Dry Granulation: Pharmaceutical Applications'. European Journal of Pharmaceutics and biopharmaceutics, 58, pp. 317-326, 2004.

Deyampert Rogers, Tracey L., 'Content Considerations for Low Dosage Drug Formulations Processed by Roller Compaction'. Ph.D. Thesis, Purdue University, Aug. 1997.

Deyampert Rogers, Tracey L., 'Oral Preliminary Examination', Sep. 1, 1995.

Falzone, Angela Marie, 'Roller Compaction of Pharmaceutical Excipients and Excipient-drug Blends'. Ph.D. Thesis, Purdue University, Dec. 1990.

Skinner, G.W., 'The Evaluation of Fine-particle Hydroxyprpycellulose as a Roller Compaction binder in Pharmaceutical Applications'. Drug Development & Indust. Pharm, 25(10), pp. 1121-1128, 1999.

The Fitzpatrick Company Europe N. V., 'Introduction to Roll Compaction and the Fitzpatrick Chilsonator'. Mar. 1997.

Sheskey, P., et al. 'Roll Compaction Granulation of a Controlled-Release Matrix Tablet Formulation Containing HPMC'. Pharmaceutical Technology, Oct. 1999.

Zhang, Y., et al., 'Physical Properties and Compact Analysis of Commonly Used Direct Compression Binders'. AAPS Pharm. Sci. Tech. 4 (4) Article 62, Dec. 15, 2003.

Hsiu-O, H. et al., 'Characteristics of Codried Products of Microcrystalline Cellulose with Saccharides and Low-substituted Hydroxypropylcellulose'. Powder Technology, 127 2002, pp. 45-53.

Gohel, M.C., 'A Review of Co-processed Directly Compressible Excipients'. Journal of Pharma, Pharma. Sci. 8(1), pp. 76-93, 2005.

Schroder, R. et al., 'Influence of Magnesium Stearate on the Compaction Behavior and Tablet characteristics of Co-Spray Dried Compounds vs Physical Blends'. Poster Presented at American Association of Pharmaceutical Science (Denver) Oct. 2001.

Jacob, S. et al. 'Novel Co-processed Excipients of Mannitol and Microcrystalline Cellulose for Preparing Fast Dissolving Tablets of Glipzide'. Indian Journal of Pharmaceutical Sciences, vol. 69 (5) Sep.-Oct. 2007, pp. 633-639.

Rowe, Sheskey & Weller, "Handbook of Pharmacuetical Excipients, Fourth Edition", 2003, Pharmaceutical Press, London. XP002281910, p. 110, col. 2.

* cited by examiner

CO-ATTRITED STABILIZER COMPOSITION

FIELD OF THE INVENTION

The present invention is directed to co-attrited stabilizer compositions that are suitable for use in, for example, aqueous food and pharmaceutical compositions, their manufacture and use.

BACKGROUND OF THE INVENTION

Microcrystalline cellulose, also known and referred to herein as "MCC," hydrolyzed cellulose wet cake, or cellulose gel, is commonly used in the food industry to enhance the properties or attributes of a final food product. For example, it has been used as a binder and stabilizer in food applications, including in beverages, as a gelling agent, a thickener, a fat substitute, and/or non-caloric filler, and as a suspension stabilizer and/or texturizer. It has also been used as a binder and disintegrant in pharmaceutical tablets, as a suspending agent in liquid pharmaceutical formulations, and as a binder, disintegrant, and processing aid in industrial applications, in household products such as detergent and/or bleach tablets, in agricultural formulations, and in personal care products such as dentifrices and cosmetics.

Microcrystalline cellulose is modified for such uses by subjecting micro-crystalline cellulose or "wet cake" to attriting processes to substantially subdivide the crystallites into finely divided particles. However, as particle size is reduced, the individual particles tend to agglomerate or hornify upon drying, a result that is undesirable in product manufacture or use. To prevent hornification, a protective colloid may be added during attrition or following attrition but before drying. The protective colloid wholly or partially neutralizes the hydrogen or other bonding forces between the smaller sized particles. The resulting materials are frequently referred to as attrited microcrystalline cellulose or colloidal microcrystalline cellulose and such attrited or colloidal microcrystalline cellulose will typically form stable suspensions with little to no settling. In contrast, non-colloidal microcrystalline cellulose will settle and not form a stable suspension in aqueous systems. Colloidal microcrystalline cellulose, such as carboxymethyl cellulose-coated microcrystalline cellulose, is described in U.S. pat. No. 3,539,365 (Durand, et al). Another colloidal microcrystalline cellulose, such as starch-coated microcrystalline cellulose, is described in US Pat. App. 2011/0151097 (Tuason et al.). FMC Corporation (Philadelphia, Pa., USA) manufactures and sells various colloidal microcrystalline cellulose products, including edible food and pharmaceutical grades, under the names of, among others, AVICEL® and GELSTAR®.

Admixtures of MCC and some hydrocolloids (such as carboxymethyl cellulose having a degree of substitution of at least 0.95, pectin, alginate, carrageenan, xanthan gum, agar gum, wellan gum, or gellan gum) may be too 'slippery' to be satisfactorily attrited. Less than satisfactory attrition of the MCC particles can have a deleterious effect on the functionality of the MCC stabilizer. As a result, some attempts have been made to solve this problem by using an attriting agent, for instance, a salt. For example, see U.S. Pat. Nos. 7,879,382, 7,462,232 and 5,366,724. Other approaches have been taken to make suitable MCC/hydrocolloid compositions. For example, see US 2005/0233046; US 2011/0151097; and WO 2010/136157.

There remains a need, however, for a co-attrited colloidal microcrystalline cellulose composition containing a carboxymethyl cellulose having a degree of substitution of at least 0.95 (such carboxymethyl celluloses being slippery). Applicants have unexpectedly found that using a carboxymethyl cellulose having a degree of substitution of from 0.95-1.5 and a viscosity of less than 100 cps is capable of being co-attrited with MCC and that such co-attrited stabilizer compositions provide superior stabilization in, for example, aqueous food systems.

SUMMARY OF THE INVENTION

The present invention is directed to a co-attrited stabilizer composition comprising: (i) microcrystalline cellulose and (ii) carboxymethyl cellulose, wherein the carboxymethyl cellulose has a degree of substitution of from 0.95-1.5 and a viscosity of less than 100 cps. The composition is useful as a stabilizer, particularly, in food and pharmaceutical applications.

The present invention is also directed to an industrial composition comprising the stabilizer of the present invention, wherein the industrial composition is, for example, a pharmaceutical composition, veterinary composition, agricultural composition, or cosmetic composition.

In addition, the present invention is directed to a method of making the stabilizer composition of the invention, comprising: a) admixing the microcrystalline cellulose and carboxymethyl cellulose of component (ii); b) co-attriting the admixture of step a); and c) drying the extrudent of step b).

DETAILED DESCRIPTION OF THE INVENTION

"Colloid" and "colloidal" are used interchangeably in the present specification to define particles that are capable of being properly suspended in an aqueous mixture. As known to those of ordinary skill in the art and referred to herein, colloidal particles may be of any suitable particle size, provided that they are able to form uniform suspensions; e.g., when measured in suspension, a majority of the particles may have a particle size of from 0.1 to 30 microns.

All viscosities of the carboxymethyl celluloses referred to herein may be measured as follows. The carboxymethyl cellulose used in the present invention is a low viscosity carboxymethyl cellulose having a degree of substitution of from 0.95-1.5 and a viscosity of less than 100 cps. The viscosity of less than 100 cps may be measured using a Brookfield Viscometer at 2% solids in water at 25° C., 60 rpm, spindle #1. "Medium viscosity" carboxymethyl cellulose as sometimes used herein refers to carboxymethyl cellulose having a range of about 200 to 4,000 cps (e.g., when measured using a Brookfield viscometer at 2% solids in water, 25° C., at 30 rpm, spindle #2). Any carboxymethyl cellulose that has higher viscosity than "medium viscosity" may be considered "high viscosity" grade carboxymethyl cellulose (and such viscosity can be measured using a Brookfield viscometer at 2% solids in water, 25° C., at 30 rpm, spindle #3 or #4).

Further, edible food products are disclosed that contain the present compositions. These food products may include aqueous systems, emulsions, beverages, sauces, soups, dressings, dairy and non-dairy milks and products, frozen desserts, and cultured foods. The edible food products can additionally comprise diverse edible material and additives, including proteins, fruit juices, vegetable juices, fruit-flavored substances, or any combination thereof. In addition, a number of industrial suspensions are disclosed that comprise the present compositions that are adapted for use in pharmaceutical products, cosmetic products, veterinary products, personal care products, agriculture products, or chemical formulations.

Microcrystalline Cellulose

Any MCC may be employed in compositions of the present invention. MCC from any source may be employed in the compositions of the present invention. Feedstocks from which MCC may be obtained include, for example, wood pulp (such as bleached sulfite and sulfate pulps), corn husks, bagasse, straw, cotton, cotton linters, flax, hemp, ramie, seaweed cellulose, and fermented cellulose. Additional feedstocks include bleached softwood kraft pulps, bleached hardwood kraft pulps, bleached Eucalyptus kraft pulps, paper pulps, fluff pulps, dissolving pulps, and bleached non-wood cellulosic pulps. In one embodiment, the MCC used is one approved for human consumption by the United States Food and Drug Administration.

The microcrystalline cellulose may be in any suitable form. The microcrystalline cellulose is preferably co-attrited in the form of a "wet cake." A microcrystalline cellulose wet cake is a microcrystalline cellulose that has been manufactured in a wet form (e.g., containing water) and has not been dried ("never dried"). In other words, a microcrystalline cellulose wet cake is microcrystalline cellulose that has not been previously dried and re-hydrated with water. Microcrystalline cellulose (MCC) may comprise tiny rod-like microcrystals of partially hydrolyzed cellulose (beta-1,4 glucan). The beta-1,4 glucan may be derived from any desired chemical degradation method applied to a selected cellulose material.

Microcrystalline cellulose is produced by treating a source of cellulose, preferably, alpha cellulose in the form of pulp from fibrous plant materials, with a mineral acid, preferably hydrochloric acid (acid hydrolysis). The acid selectively attacks the less ordered regions of the cellulose polymer chain thereby exposing and freeing the crystalline sites which form crystallite aggregates which constitute the microcrystalline cellulose. These are then separated from the reaction mixture, and washed to remove degraded by-products. The resulting wet mass, generally containing 40 to 60 percent moisture, is referred to in the art by several names, including 'hydrolyzed cellulose', 'hydrolyzed cellulose wet cake', 'level-off DP cellulose', 'microcrystalline cellulose wet cake', or simply 'wet cake'.

The classic process for MCC production is acid hydrolysis of purified cellulose, pioneered by O. A. Battista (U.S. Pat. Nos. 2,978,446; 3,023,104; and 3,146,168). Various chemical or mechanical treatments may be used to enhance the MCC acid hydrolysis. In efforts to reduce the cost while maintaining or improving the quality of MCC, various alternative processes have also been proposed. Among these are steam explosion (U.S. Pat. No. 5,769,934; Ha et al.), reactive extrusion (U.S. Pat. No. 6,228,213; Hanna et al.), one-step hydrolysis and bleaching (World Patent Publication WO 01/0244; Schaible et al.), and partial hydrolysis of a semi-crystalline cellulose and water reaction liquor in a reactor pressurized with oxygen and/or carbon dioxide gas and operating at 100° C. to 200° C. (U.S. Pat. No. 5,543,511).

Carboxymethyl Cellulose

The carboxymethyl cellulose used in the present invention in component (ii) is very specific and has a degree of substitution of from 0.95 to 1.5 and a viscosity of less than 100 cps. Such a carboxymethyl cellulose is considered in the field to have a high degree of substitution and a very low viscosity (and, as such, is sometimes referred to herein as a "high DS/low viscosity CMC"). In more particular embodiments, the degree of substitution may be from 1.0-1.5, more specifically, 1.0-1.4, and 1.1-1.3; and the viscosity may be from 2 to 100 cps, more specifically, from 2 to 50 cps, from 2 to 35 cps, from 2 to 30 cps, and from 2 to 25 cps.

Such a carboxymethyl cellulose can be an alkali metal carboxymethyl cellulose, more particularly sodium, potassium, or ammonium carboxymethyl cellulose, and most preferably sodium carboxymethyl cellulose.

Carboxymethyl cellulose is characterized by, inter alia, the degree of substitution (sometimes referred to herein as "DS"). The DS represents the average number of hydroxyl groups substituted per anhydroglucose unit. For example, each anhydroglucose unit in carboxymethyl cellulose contains three hydroxyl groups, which gives carboxymethyl cellulose a maximum theoretical DS of 3.0.

Commercially available carboxymethyl cellulose having a DS of from 0.95-1.5 is Ambergum 1221 (Ashland; a low viscosity carboxymethyl cellulose having a DS of about 1.2).

Preferably, the co-attrited stabilizer composition of the present invention additionally comprises component (iii) at least one of a carboxymethyl cellulose having a degree of substitution of less from 0.45 to 0.9 or a carboxymethyl cellulose having a DS of from 0.95 to 1.5 and a viscosity of 200-4,000 cps. Such carboxymethyl celluloses also include the alkali metal salts thereof such as sodium, potassium or ammonium carboxymethyl cellulose. The carboxymethyl cellulose of component (iii) can have a medium viscosity of from 200 cps to 4000 cps, preferably 200 cps to 1000 cps, with a DS between 0.45 to about 0.9. One particular example of this low DS-medium viscosity CMC is Aqualon 7MF series from Ashland. The carboxymethyl cellulose of component (iii) can also have a low viscosity of from 5 cps to 200 cps, preferably 5 cps to 100 cps, with DS between 0.45 to about 0.9. One particular example of this low DS-low viscosity CMC is Aqualon 7LF from Ashland. In addition, the carboxymethyl cellulose of component (iii) may also have a viscosity of from 200 cps to 4000 cps, preferably 200 cps to 1000 cps, with DS between about 0.95 to about 1.5. Particular examples of such high DS-medium viscosity CMCs include Aqualon 12M8F and 12M31P, all from Ashland.

Generally, the microcrystalline cellulose is present in an amount of from 60-96%, more preferably, 80-95%, more preferably, 80-90%, all based on the total weight of the microcrystalline cellulose and carboxymethyl cellulose of component (ii), and the carboxymethyl cellulose of component (ii) is present in an amount of from 4-40%, more preferably, 5-20%, more preferably, 10-20%, all based on the total weight of the microcrystalline cellulose and carboxymethyl cellulose of component (ii). Further, if the carboxymethyl cellulose of component (iii) is present, then the carboxymethyl cellulose of component (iii) may be present in an amount of from 2-36%, more preferably, 2-20%, more preferably, 2-15%, all based on the total weight of the stabilizer composition.

The stabilizer compositions may consist only of the MCC in component (i) and the carboxymethyl cellulose of component (ii). Also, the stabilizer compositions may consist only of the MCC in component (i), the carboxymethyl cellulose of component (ii) and the carboxymethyl cellulose of component (iii). The co-attrited stabilizer composition of the present invention may contain less than 5% starch, less than 4% starch, less than 3% starch, less than 2% starch, less than 1% starch, all based on the total weight of the stabilizer or contain no starch. In addition, the stabilizer composition of the present invention may or may not include any attriting aid such as a salt.

Historically, when attempts were made to make colloidal MCC with high DS (i.e., 0.9-1.5)/medium viscosity (200-4, 000 cps), the attrition between MCC and CMC would be very slippery, unable to generate adequate work profile. Tests also showed unsatisfactory performance in food applications. It was discovered by the present inventors that if high DS-low viscosity CMC is used in the MCC/CMC attrition/extrusion, the behavior changed significantly as opposed to using high DS-medium or high viscosity CMC. The resulting colloidal MCC/CMC of the present invention had excellent performance in food applications, such as in soy beverages. More synergy in attrition/extrusion was discovered with the addition of a second CMC, which contributed to the outstanding food performance as well.

Co-Attriting

The present invention is also directed to a method of making the stabilizer composition of the present invention, comprising: a) admixing the microcrystalline cellulose and carboxymethyl cellulose of component (ii); b) co-attriting the admixture of step a); and c) drying the extrudent of step b). The carboxymethyl cellulose of component (iii), if present, is added into step a). As used herein, the terms "co-attrited", "attrited" and "attrition" are used interchangeably to mean a process that effectively reduces the size of at least some if not all of the particles to a colloidal size. "Co-attrition" is a term used to refer to the application of shear forces to an admixture of components. Suitable attrition processes may be accomplished, for example, by co-extruding, milling, admixing, or kneading. The MCC is typically wet cake having a solids level of between 35%70%, but it can be used in dried or re-hydrated form. In addition to various types of extruders as practiced in current MCC manufacturing, other examples of equipment for attriting wetcake or MCC:CMC include compression rolls/belts, calendaring rolls, mechanical refiner discs, ultrasonic refiners, high pressure homogenizers (including Microfluidic devices), high compression planetary mixers, and shockwave/cavitation devices. The drying may be carried out by a variety of means, such as by spray drying, oven drying, freeze drying, drum drying, flash drying, fluidized bed, vacuum drying, bulk drying, or thermal reactor drying. The drying removes water from the composition to obtain a product that would be recognized by one skilled in the art as a "dried" product. For spray drying, the extrudent is dispersed in water to form a slurry, optionally homogenized, and then spray dried. Dry particles formed from the spray drying can be reconstituted in a desired aqueous medium or solution to form the compositions, edible food products, and industrial application suspensions described herein.

Formulations Using the Stabilizer Composition

The co-attrited stabilizer compositions of the present invention can act as stabilizers in a variety of industrial and consumer uses. In particular, these applications include food (e.g., beverage), pharmaceutical, health care, agrochemical and other industrial applications.

The stabilizer compositions, after drying to powder form, can be mixed with an aqueous solution to form a stable colloidal suspension. The edible food products formed using the stabilizer compositions described herein are capable of providing stable colloidal properties for extended periods even at acidic pH conditions.

Some examples of the edible food products include the following: suspensions, sauces (especially low pH/high salt types), retorted soups, dressings (including both spoonable and pourable dressings), beverages (including those that are heat treated, for example, by pasteurization or ultra pasteurization, or heat treated using ultra high temperature (UHT) or high temperature short time (HTST) or retort processes, UHT and retort processed protein and nutritional beverages, UHT processed low pH protein-based beverages, UHT Calcium fortified beverages, UHT milk-based beverages), UHT and retort processed milk creams, low pH frozen desserts (e.g., fruit sherbets), aerated food systems, dairy and non-dairy based, cultured products (sour cream, yogurts), and bakery fillings or creams. More specific examples of beverages containing the stabilizer composition of the invention include dairy beverages, e.g., dairy beverages containing milk (including low and no fat milk) and flavored milks such as chocolate milk and strawberry milk, as well as containing plant proteins such as soy protein and nut protein.

The use levels of the stabilizer compositions in food products can range from about 0.05% to about 3.5% by weight of total food product, and in some instances can be 0.2% to 2% by weight of total food product.

The food products can also include other edible ingredients such as, for example, vegetable or fruit pulps, mineral salts, protein sources, fruit juices, acidulants, sweeteners, buffering agents, pH modifiers, stabilizing salts, or a combination thereof. Those skilled in the art will recognize that any number of other edible components may also be added, for example, additional flavorings, colorings, preservatives, pH buffers, nutritional supplements, process aids, and the like. The additional edible ingredients can be soluble or insoluble, and, if insoluble, can be suspended in the food product.

Some of the edible food products that may contain the stabilizer composition of the invention may comprise protein and/or fruit juice (e.g., fruit juices containing solids (such as pulp) and nectars are readily stabilized by adding the stabilizer compositions). In such blends having only juice or only protein, the composition of the stabilizer composition and the amount of stabilizer composition used in the beverage blend may need to be adjusted accordingly to maintain the desired stability results. Such routine adjustment of the composition is fully within the capabilities of one having skill in the art and is within the scope and intent of the present invention. These edible food products can be dry mix products (instant sauces, gravies, soups, instant cocoa drinks, etc.), low pH dairy systems (sour cream/yogurt, yogurt drinks, stabilized frozen yogurt, etc.), baked goods, and a bulking agent in non-aqueous food systems and in low moisture food systems.

Suitable juices incorporating the stabilizer composition include fruit juices (including but not limited to lemon juice, lime juice, and orange juice, including variations such as lemonade, limeade, or orangeade, white and red grape juices, grapefruit juice, apple juice, pear juice, cranberry juice, blueberry juice, raspberry juice, cherry juice, pineapple juice, pomegranate juice, mango juice, apricot juice or nectar, strawberry juice, kiwi juice) and vegetable juices (including but not limited to tomato juice, carrot juice, celery juice, beet juice, parsley juice, spinach juice, and lettuce juice). The juices may be in any form, including liquid, solid, or semi-solid forms such as gels or other concentrates, ices or sorbets, or powders, and may also contain suspended solids.

In another embodiment, fruit-flavored or other sweetened substances, including naturally flavored, artificially flavored, or those with other natural flavors ("WONF"), may be used instead of fruit juice. Such fruit flavored substances may also be in the form of liquids, solids, or semi-solids, such as powders, gels or other concentrates, ices, or sorbets, and may also contain suspended solids.

Proteins suitable for the edible food products incorporating the stabilizer compositions include food proteins and amino acids, which can be beneficial to mammals, birds, reptiles, and fish. Food proteins include animal or plant proteins and fractions or derivatives thereof. Animal derived proteins include milk and milk derived products, such as heavy cream, light cream, whole milk, low fat milk, skim milk, fortified milk including protein fortified milk, processed milk and milk products including superheated and/or condensed, sweetened or unsweetened skin milk or whole milk, dried milk powders including whole milk powder and nonfat dry milk (NFDM), casein and caseinates, whey and whey derived products such as whey concentrate, delactosed whey, demineralized whey, whey protein isolate. Egg and egg-derived proteins may also be used. Plant derived proteins include nut and nut derived proteins, sorghum, legume and legume derived proteins such as soy and soy derived products such as untreated fresh soy, fluid soy, soy concentrate, soy isolate, soy flour, and rice proteins, and all forms and fractions thereof. Food proteins may be used in any available form, including liquid, condensed, or powdered. When using a powdered protein source, however, it may be desirable to prehydrate the protein source prior to blending with stabilizer compositions and juice for added stability of the resulting beverage. When protein is added in conjunction with a fruit or vegetable juice, the amount used will depend upon the desired end result. Typical amounts of protein range from about 1 to about 20 grams per 8 oz. serving of the resulting stable edible food products, such as beverages, but may be higher depending upon the application.

Other products and applications for which the present compositions, or stabilizer compositions, may be used include industrial suspensions. In some embodiments, the industrial suspensions include the present compositions that are adapted for use in pharmaceuticals, cosmetics, personal care products, agricultural products, or chemical formulations. Some examples of applications include use as an excipient for oral dose forms such as tablets and chewable tablets, taste masking for drug actives (such as APAP, aspirin, ibuprofen, etc.); suspending agent; controlled release agent in pharmaceutical applications; delivery system for flavoring agents and nutraceutical ingredients in food, pharmaceutical, and agricultural applications; direct compression sustained release agent, which can be used in pharmaceutical dosage forms such as tablets, films, and suspensions; thickener, which can be used in foams, creams, and lotions for personal care applications; suspending agent, which can be used with pigments and fillers in ceramics, colorants, cosmetics, and oral care; material in ceramics; delivery system for pesticides including insecticides and other agricultural products.

As controls used in the examples below, co-attrited commercially available MCC and high DS-medium viscosity CMC (with or without a second CMC) were tested in the examples below, under the identical extrusion conditions of the present invention. All the commercial control samples failed chocolate food tests. Also shown by the examples below are the commercial colloidal MCC products comprising other high DS CMCs (but with higher viscosities) in comparison with the present invention in food application performance.

Further, as demonstrated in the examples below, as the CMC viscosity goes beyond 200 cps into the high DS-medium viscosity range, as shown by the controls (Examples 15-16), the samples made under the control attrition/extrusion conditions failed immediately in the food tests.

If desired, dry powders of colloidal MCC/CMC (such as Avicel® CL611 or Avicel® RC591) may be added to the MCC/High DS CMC admixture and attrited/extruded together to generate food functioning products as shown in one of the examples below. An additional strategy to aid the attrition may include co-attriting/co-extruding with direct cooling by adding dry ice (frozen CO2), liquid nitrogen, liquid ammonia, etc. Another approach includes the addition/dissolution of ammonium salts into the MCC/High DS CMC admixture, which will cool down the admixture (especially during attrition or extrusion), as well as make the extrudate easier to attrite or extrude. Ammonium salts may also depress the dispersion viscosity, facilitating drying at higher solids in spray-drying. If bulk drying, the colloidal MCC product would be fluffier and more porous (due to decomposition/puff of ammonium salts). Finally, there is an added benefit that the ammonium salts will puff and leave no salt residual in the final product. The ammonium salts may include any water soluble inorganic salts, such as, but not limited to, ammonium carbonate, ammonium bicarbonate, ammonium chloride, ammonium sulfates, and ammonium phosphates, etc. The ammonium salts may also include any water soluble organic salts, such as, but not limited to, ammonium acetate, ammonium citrate, ammonium lactate, ammonium formate, ammonium tartate, ammonium oxalate, and ammonium ascorbate, etc. Ammonium bicarbonate and ammonium carbonate are the preferred salts.

Other features and advantages of the foregoing embodiments will be apparent from the following detailed description and from the claims. The disclosed embodiments are exemplary and explanatory only and not to be considered to be restrictive of the invention. Unless otherwise indicated herein, all parts, percents, ratios and the like are by weight.

EXAMPLES

The Brookfield viscosities of the co-attrited compositions tested below were obtained using a RVT viscometer with an appropriate spindle (typically between 1-4) at 20 rpm and at 20° to 23° C. The viscosities were measured to determine an initial viscosity and a set up viscosity after 24 hours.

"Gel strength (G')" refers to the reversibly stored energy of the system (the elastic modulus G') and relative to the compositions herein is a function of the cellulose concentration. The measurements in the examples were made using a TA-Instruments rheometer (ARES-RFS3) with oscillatory strain sweep at 1 Hz and at 20° C., with gap size at 1.8 mm in a 2.6% solids water (de-ionized) dispersion after 24 hours.

Examples 1-7

MCC/High DS CMC with Low Viscosities <25 cps, Ambergum 1221

Example 1

MCC Attrited with High DS-Low Viscosity CMC

MCC wetcake was obtained by acid hydrolysis. It was dewatered to a solids level of 41.6%. In a Hobart mixer, the MCC wetcake was admixed with Ambergum 1221 CMC (Ashland, Inc., Wilmington, Del., USA) in a ratio of 85:15 parts by weight for several minutes. The admixture was passed through a co-rotating twin-screw extruder several times with sufficient work profile. The MCC:CMC extrudate was then dispersed in deionized water. The resulting slurry was passed through a Manton Gaulin homogenizer at 2500 to 3000 psi and spray dried on a 3 foot spray dryer to form a powder. When the dried MCC:CMC powder was redispersed in deionized water, at 2.6% solids, it exhibited at room temperature an initial Brookfield viscosity of 520 cps and a set-up viscosity after 24 hrs of 1,030 cps.

Example 2

MCC Attrited with High DS-Low Viscosity CMC (Ambergum 1221)

This test was generally conducted as in Example 1, except the MCC:CMC ratio was 80%:20% and the MCC wetcake solids level was dewatered to about 42%. When the dried MCC:CMC powder was redispersed in deionized water, at 2.6% solids, it exhibited at room temperature an initial Brookfield viscosity of 280 cps and a set-up viscosity after 24 hrs of 680 cps. The 2.6% solids dispersion was measured after 24 hrs and exhibited a gel strength G' of 18 Pa. A colloidal content of 64.2% was obtained.

Example 3

MCC Co-Attrited with High DS-Low Viscosity CMC (Ambergum 1221) and Low DS-Low Viscosity CMC (7LF)

MCC was co-attrited with two types of CMCs: Ambergum 1221 (high DS, low viscosity CMC) and Aqualon 7LF CMC (a low DS, low viscosity CMC). The MCC:CMC ratio was 80% MCC:14% Ambergum1221:6% Aqualon 7LF CMC. MCC wetcake was obtained by acid hydrolysis. It was dewatered to a solids level of 41.6%. In a Hobart mixer, the MCC wetcake was admixed with Ambergum 1221 CMC (Ashland, Inc., Wilmington, Del., USA) as well as Aqualon 7LF CMC in a ratio of 80:14:6 parts by weight for several minutes. The admixture was passed through a co-rotating twin-screw extruder several times with sufficient work profile. The MCC:CMC extrudate was then dispersed in deionized water. The resulting slurry was then spray dried on a 3 foot spray dryer to form a powder. When the spray-dried MCC:CMC powder was redispersed in deionized water, at 2.6% solids, it exhibited at room temperature an initial Brookfield viscosity of 1,000 cps and a set-up viscosity after 24 hrs of 3,000 cps. The 2.6% solids dispersion was measured after 24 hrs and exhibited a gel strength G' of 50 Pa. A colloidal content of 85.7% was obtained.

Example 4

MCC Co-Attrited with High DS-Low Viscosity CMC (Ambergum 1221) and Low DS-Low Viscosity CMC (7LF)

This test was conducted as in Example 3, except the MCC:CMC ratio was 84% MCC:12% Ambergum1221:4% Aqualon 7LF CMC. When the dried MCC:CMC powder was redispersed in deionized water, at 2.6% solids, it exhibited at room temperature an initial Brookfield viscosity of 1,000 cps and a set-up viscosity after 24 hrs of 2,600 cps.

Example 5

MCC Co-Attrited with High DS-Low Viscosity CMC (Ambergum 1221) and Low DS-Medium Viscosity CMC (7MF)

This test was conducted as in Example 3, except the MCC:CMC ratio was 80% MCC:14% Ambergum1221:6% Aqualon 7MF CMC. When the dried MCC:CMC powder was redispersed in deionized water, at 2.6% solids, it exhibited at room temperature an initial Brookfield viscosity of 3,400 cps and a set-up viscosity after 24 hrs of 3,600 cps. The 2.6% solids dispersion was measured after 24 hrs and exhibited a gel strength G' of 100 Pa. A colloidal content of 91.1% was obtained.

Example 6

MCC Co-Attrited with High DS-Low Viscosity CMC (Ambergum 1221) and Low DS-Medium Viscosity CMC (7MF)

This test was conducted as in Example 3, except the MCC:CMC ratio was 80% MCC:15% Ambergum1221:5% Aqualon 7MF CMC. When the dried MCC:CMC powder was redispersed in deionized water, at 2.6% solids, it exhibited at room temperature an initial Brookfield viscosity of 2,425 cps and a set-up viscosity after 24 hrs of 4,000 cps.

Example 7

MCC Co-Attrited with High DS-Low Viscosity CMC (Ambergum 1221) and Low DS-Medium Viscosity CMC (7MF)

MCC was co-attrited with two types of CMCs: Ambergum 1221 (high DS, low viscosity CMC) and Aqualon 7MF CMC III (a low DS, medium viscosity CMC). The MCC:CMCs ratio was 80% MCC:15% Ambergum1221:5% Aqualon 7MF CMC. MCC wetcake was obtained by acid hydrolysis. It was then mixed and extruded in a pilot scale set-up of a co-rotating twin-screw extruder. The MCC:CMC extrudate was then dispersed in deionized water. The resulting slurry was then spray dried to form a powder. When the spray-dried MCC:CMC powder was redispersed in deionized water, at 2.6% solids, it exhibited at room temperature an initial Brookfield viscosity of 1,800 cps and a set-up viscosity after 24 hrs of 3,150 cps. The 2.6% solids dispersion was measured after 24 hrs and exhibited a gel strength G' of 55 Pa.

Examples 8-12

MCC/High DS CMC with Low Viscosities >25 cps, <100 cps

Example 8

MCC Attrited with High DS-Low Viscosity CMC (Aqualon 12LF#17)

The high DS low viscosity CMC used in this example had a viscosity of 38 cps and DS 1.28 (Aqualon 12LF#17). This test was conducted as in Example 2, except the MCC:CMC ratio was 80% MCC:20% Aqualon 12LF CMC. When the spray-dried MCC:CMC powder was redispersed in deionized water, at 2.6% solids, it exhibited at room temperature an initial Brookfield viscosity of 800 cps and a set-up viscosity after 24 hrs of 850 cps. A colloidal content of 37% was obtained.

Example 9

MCC Co-Attrited with High DS-Low Viscosity CMC (Aqualon 12LF#17) and Low DS-Low Viscosity CMC (7LF)

MCC was co-attrited with two types of CMCs: Aqualon 12LF#17 (1.28 DS, viscosity 38 cps) and Aqualon 7LF CMC (a low DS, low viscosity CMC). The MCC:CMC ratio was 80% (MCC):14% (Aqualon 12LF#17):6% (Aqualon 7LF CMC). MCC wetcake was obtained by acid hydrolysis cooking. It was dewatered to a solids level of 41.6%. In a Hobart mixer, the MCC wetcake was admixed with Aqualon 12LF#17 CMC (Ashland, Inc., Wilmington, Del., USA) as well as Aqualon 7LF CMC in a ratio of 80:14:6 parts by weight for several minutes. The admixture was passed through a co-rotating twin-screw extruder several times with sufficient work profile. The MCC:CMC extrudate was then dispersed in deionized water. The resulting slurry was then spray dried on a 3 foot Bowen spray dryer to form a powder. When the spray-dried MCC:CMC powder was redispersed in deionized water at 2.6% solids, it exhibited at room temperature an initial Brookfield viscosity of 600 cps and a set-up viscosity after 24 hrs of 2,050 cps. A colloidal content of 61.5% was obtained.

Example 10

MCC Co-Attrited with High DS-Low Viscosity CMC (Aqualon 12LF#24) and Low DS-Low Viscosity CMC (7LF)

MCC was co-attrited with two types of CMCs: Aqualon 12LF#24 (1.30 DS, viscosity 36 cps) and Aqualon 7LF CMC (a low DS, low viscosity CMC). The MCC:CMC ratio was 80% (MCC):14% (Aqualon 12LF#24):6% (Aqualon 7LF CMC). MCC wetcake was obtained by acid hydrolysis. It was dewatered to a solids level of 41.6%. In a Hobart mixer, the MCC wetcake was admixed with Aqualon 12LF#24 CMC (Ashland, Inc., Wilmington, Del., USA) as well as Aqualon 7LF CMC in a ratio of 80:14:6 parts by weight for several minutes. The admixture was passed through a co-rotating twin-screw extruder several times with sufficient work profile. The MCC:CMC extrudate was then dispersed in deionized water. The resulting slurry was then spray dried on a 3 foot Bowen spray dryer to form a powder. When the spray-dried MCC:CMC powder was redispersed in deionized water at 2.6% solids, it exhibited at room temperature an initial Brookfield viscosity of 275 cps and a set-up viscosity after 24 hrs of 1,600 cps. A colloidal content of 55.7% was obtained.

Example 11

MCC Attrited with Other Type of High DS-Low Viscosity CMC (Aqualon 12LF#24)

This test was conducted in the identical way as in Example 2, except the MCC:CMC ratio was 85% MCC:15% Aqualon 12LF#24 CMC and during the extrusion, dry ice (30% by weight of the extrudate dry weight) was added to cool the extrudate directly. When the spray-dried MCC:CMC powder was redispersed in deionized water at 2.6% solids, it exhibited at room temperature an initial Brookfield viscosity of 1,000 cps and a set-up viscosity after 24 hrs of 1,125 cps.

Example 12

MCC:High DS-Low Viscosity CMC (Aqualon 12LF#24)

MCC was co-attrited with Aqualon 12LF#24 (1.30 DS, viscosity 36 cps) and dry powder of Avicel® RC-591. The use of dry powder of Avicel® RC591 enhanced the extrusion intensity. MCC wetcake was obtained by acid hydrolysis. It was dewatered to a solids level of 41.6%. In a Hobart mixer, the MCC wetcake was admixed with Aqualon 12LF#24 CMC (Ashland, Inc., Wilmington, Del., USA) as well as Avicel® RC-591 in a ratio of 64:16:20 parts by weight, respectively, for several minutes. The admixture was passed through a co-rotating twin-screw extruder several times with sufficient work profile. The resulting extrudate was then dispersed in deionized water. The resulting slurry was then spray dried on a 3 foot spray dryer to form a powder. When the spray-dried powder was redispersed in deionized water at 2.6% solids, it exhibited at room temperature an initial Brookfield viscosity of 2,750 cps and a set-up viscosity after 24 hrs of 2,600 cps. A colloidal content of 86.9% was obtained.

Example 13

MCC Co-Attrited with High DS-Low Viscosity CMC (Ambergum 1221) and High DS-Medium Viscosity CMC (12M8F)

This test was conducted as in Example 3, except the MCC:CMC ratio was 80% MCC:14% Ambergum1221:6% Aqualon 12M8F CMC. When the dried MCC:CMC powder was redispersed in deionized water at 2.6% solids, it exhibited at room temperature an initial Brookfield viscosity of 1,000 cps and a set-up viscosity after 24 hrs of 1,500 cps. A colloidal content of 64.9% was obtained.

Comparative Examples (14-17)

Example 14

MCC Attrited with High DS Medium Viscosity CMC (12M8F) under Control Conditions

MCC wetcake was obtained by acid hydrolysis. It was dewatered to a solids level of 41.6%. In a Hobart mixer, the MCC wetcake was admixed with Aqualon 12M8F CMC (Ashland, Inc., Wilmington, Del., USA) in a ratio of 80:20 parts by weight for several minutes. The admixture was passed through a co-rotating twin-screw extruder several times. The MCC:CMC extrudate was then dispersed in deionized water. The resulting slurry was then spray dried on a 3 foot spray dryer to form a powder. When the spray-dried MCC:CMC powder was re-dispersed in deionized water at 2.6% solids, it exhibited at room temperature an initial Brookfield viscosity of 740 cps and a set-up viscosity after 24 hrs of 1,080 cps. Food test in chocolate milk failed immediately, due to heavy sedimentation.

Example 15

MCC Co-Attrited with High DS Medium Viscosity CMC (12M8F) and Low DS CMC, under Control Conditions The experiment was conducted in a similar way as in Example 14, except two types of CMC were used during co-attrition/extrusion. The ratio was 80% MCC:10%12M8F:10% 7LF CMC. When the spray-dried MCC:CMC powder was re-dispersed in de-ionized water at 2.6% solids, it exhibited at room temperature an initial Brookfield viscosity of 67 cps and a set-up viscosity after 24 hrs of 1,260 cps. Food test in chocolate milk failed immediately, due to heavy sedimentation and phase separation.

Example 16

Commercial Colloidal MCC Comprising High DS, Medium Viscosity CMC and Salt

A commercially available colloidal MCC comprising high DS, medium viscosity CMC and salt (as attriting aid) was dispersed in deionized water at 2.6% solids. It exhibited at room temperature an initial Brookfield viscosity of 1,650 cps and a set-up viscosity after 24 hrs of 3,250 cps. A colloidal content of 80% was obtained, which was determined by centrifugation of the water dispersion at 8,250 rpm for 15 minutes followed by gravimetric analysis of the dried supernatant portion. This commercially available stabilizer is considered to be among the best performers and is used herein as a benchmark to compare the performance of the stabilizers of the present invention (using a different CMC and no attriting aid).

Example 17

Commercial Colloidal MCC Comprising Low DS CMC (i.e., Avicel® RC-591)

When dispersed in deionized water at 1.2% solids, this sample exhibited at room temperature an initial Brookfield viscosity of 40-175 cps and a set-up viscosity after 24 hrs of 800 to 1,600 cps.

Examples 18-21

Food Applications

Example 18

UHT Chocolate Milk Beverages

Materials and Methods:

Samples of UHT chocolate beverages were prepared using: A) commercial colloidal MCC/high DS, medium viscosity CMC as described in Example 16 (control sample); B) colloidal MCC/high DS-low viscosity CMC as in Example 2 (inventive sample); C) colloidal MCC/mix of high DS-low viscosity CMC and low DS-low viscosity CMC as in Example 3 (inventive sample); D) colloidal MCC/mix of high DS-low viscosity CMC and low DS-low viscosity CMC as in Example 4 (inventive sample); E) colloidal MCC/mix of high DS-low viscosity CMC and high DS-medium viscosity CMC as in Example 13 (inventive sample). The formulations are shown in Table 1.

TABLE 1

| Ingredients | Sample A % by wt | Sample B % by wt | Sample C % by wt | Sample D % by wt | Sample E % by wt |
|---|---|---|---|---|---|
| Milk - 1.0% Fat | 91.35 | 91.35 | 91.35 | 91.35 | 91.35 |
| Sugar | 7.500 | 7.500 | 7.500 | 7.500 | 7.500 |
| Cocoa Powder | 0.9 | 0.9 | 0.9 | 0.9 | 0.9 |
| Sample A | 0.25 | | | | |
| Sample B | | 0.25 | | | |
| Sample C | | | 0.25 | | |
| Sample D | | | | 0.25 | |
| Sample E | | | | | 0.25 |
| Total | 100 | 100 | 100 | 100 | 100 |

Process:

All powders were dry blended together and mixed for 30 minutes with the milk using a simple overhead mixing apparatus (Lightnin Mixer). Each sample was processed through a Micro Thermics® UHT/HTST Direct & Indirect Processing System assembled to deliver the following temperature sequences and holding time. The unprocessed mixture was first preheated to 185° F. followed by immediate indirect steam sterilization in the final heater. The resulting product was held at 284° F. for 6 seconds followed by cooling to 150° F. Two-stage homogenization was employed (2,500 first stage/500 psi $2^{nd}$ stage). The sterilized mix was further cooled to ~70° F. where the product was filled into ¼ litre clear nalgene bottles inside of a Clean-Fill Hood & Sterile Product Outlet. One set of bottles was place in cold storage @40° F. and the second set was placed on a shelf at ambient temperatures (70° F.). Beverages were analyzed for viscosity, pH, and physical stability @1 day, 1 week, 2 weeks, 1 month, and 3 month shelf-life. Each testing period consisted of the following observations.

TABLE 2

| Visual Parameters | | |
|---|---|---|
| Visual Parameters | Explanation | Standard Scale to be used |
| In the 250 ml bottle before any manipulation | | |
| Creaming | Fat separation at the top | 0 = absence; 1 = 0.5 mm; 2 = 0.5 to 1 mm; 3 = 1 to 2 mm; 4 >2 mm. |
| Clear Top Separation | Visual Transparent Layer at the Top | 0 = absence; 1 = >0-2 mm; 2 = >2-4 mm; 3 = >4-6 mm; 4 = >6 mm. |
| Marbling | Clear Layers of Whey Inside the Product (waves) | 0 = absence; 1 = very slight marbling; 2 = slight marbling; 3 = strong marbling (not acceptable); 4 = very strong marbling (not acceptable). |
| Sedimentation Layer | Cocoa or Particles Layer at the Bottom of the Liquid | 0 = absence; 1 = 0.5 mm; 2 = 0.5 to 1 mm; 3 = 1 to 2 mm; 4 >2 mm. |
| In a 250 ml glass beaker or cylinder during and after pouring | | |
| Flow Properties | During pouring evaluate level of ripple until gelled pieces are visible. | 0 = absence of ripple; 1 = slight ripple; 2 = ripple; 3 = strong ripple, makes noise while pouring (not acceptable); 4 = gelled pieces (not acceptable). |
| Sedimentation at the bottom | After pouring, proteins or particles (e.g., cocoa, calcium) are visible at the bottom of the bottle. | 0 = absence of sedimentation; 1 = very slight sedimentation; 2 = slight sedimentation; 3 = strong sedimentation (not acceptable); 4 = very strong sedimentation (not acceptable). |
| Re-dispersibility | Evaluation of the possibility to re-disperse the sedimentation of proteins or particles (e.g., calcium, cocoa, etc.) when the product is poured multiple times. | 0 = absence of sedimentation; 1 = sedimentation disappears after 1 time redispersing (=2 times poured); 2 = sedimentation disappears after 2 times redispersing; 3 = sedimentation disappears after 3 times redispersing; 4 = sedimentation disappears after 4 times redispersing. |

TABLE 3

| | One Month Observation | | | | |
|---|---|---|---|---|---|
| | Sample A | Sample B | Sample C | Sample D | Sample E |
| Ambient storage viscosity* | 12.5 | 10.5 | 12.5 | 18 | 11 |
| Refrigerated viscosity# | 16 | 11 | 11 | 16 | 11.5 |

TABLE 3-continued

One Month Observation

|  | Sample A | Sample B | Sample C | Sample D | Sample E |
|---|---|---|---|---|---|
| Sedimentation layer | none | None | none | none | None |
| Other observations |  | Slight marbling at 40 F. |  |  |  |

*Viscosity determined using an LVF Brookfield Viscometer at 60 rpm, spindle #1 at 70° F.
Viscosity determined using an LVF Brookfield Viscometer at 60 rpm, spindle #1 at 40° F.

Conclusion (one month observation): Visual defects associated with instability in chocolate beverages are often observed within the first few hours after filling the containers. In UHT chocolate milk applications stabilized with colloidal microcrystalline cellulose, the most prominent sign of instability is the sedimentation of the cocoa particles. The commercial Sample A used as a control and a benchmark consistently provided excellent suspension of the cocoa particles with minimal viscosity and no signs of gelation. Inventive samples B, C, D, and E were unexpectedly found to provide equivalent stability characteristics as the control Sample A revealing no signs of sedimentation and no visual signs of gelation. Among these samples in the case of refrigerated conditions, Sample B showed some slight marbling, but was still effective. Samples C, D, and E had ideal stabilization. These results indicate that the stabilizer of the present invention provided an unexpected level of stabilization and was comparable to a high performing commercial product. The additional tests that were performed as set forth in Table 2 showed no defects for samples A-E.

Example 19

UHT Chocolate Milk Beverages

Materials and Methods:

Samples of UHT chocolate beverages were prepared using A) commercial colloidal MCC/high DS, medium viscosity CMC as described in Example 16 (control sample); B) colloidal MCC/mix of high DS-low viscosity CMC and low DS-medium viscosity CMC as in Example 6 (inventive sample); C) pilot scale-made colloidal MCC/mix of high DS-low viscosity CMC and low DS-medium viscosity CMC as in Example 7 (inventive sample). The formulations are shown in Table 4.

TABLE 4

| Ingredients | Sample A % by wt | Sample B % by wt | Sample C % by wt |
|---|---|---|---|
| Milk - 1.0% Fat | 91.35 | 91.35 | 91.35 |
| Sugar | 7.500 | 7.500 | 7.500 |
| Cocoa Powder | 0.9 | 0.9 | 0.9 |
| Sample A | 0.25 |  |  |
| Sample B |  | 0.25 |  |
| Sample C |  |  | 0.25 |
| Total | 100 | 100 | 100 |

Process:

All powders were dry blended together and mixed for 30 minutes with the milk using a simple overhead mixing apparatus (Lightnin Mixer). Each sample was processed through a Micro Thermics® UHT/HTST Direct & Indirect Processing System assembled to deliver the following temperature sequences and holding time. The unprocessed mixture was first preheated to 185° F. followed by immediate indirect steam sterilization in the final heater. Product was held at 284° F. for 6 seconds followed by cooling to 150° F. Two-stage homogenization was employed (2,500 first stage/500 psi $2^{nd}$ stage). The sterilized mix was further cooled to ~70° F. where the product was filled into ¼ litre clear nalgene bottles inside of a Clean-Fill Hood & Sterile Product Outlet. One set of bottles was place in cold storage @40° F. and the second set was placed on a shelf at ambient temperatures (70° F.). Beverages were analyzed for viscosity, pH, and physical stability. Visual parameters and scale are described in Table 2.

TABLE 5

One Week Observation

|  | Sample A | Sample B | Sample C |
|---|---|---|---|
| Ambient storage viscosity* | 10 | 19 | 14 |
| Refrigerated viscosity# | 13 | 21 | 14 |
| Sedimentation layer | #1 | none | None |
| Other observations | No defect | No defect | No defect |

*Viscosity determined using an LVF Brookfield Viscometer at 60 rpm, spindle #1 at 70° F.
Viscosity determined using an LVF Brookfield Viscometer at 60 rpm, spindle #1 at 40° F.

Conclusion (one week observation): Sample A provided good stability with no signs of gelation and very slight (but acceptable) sedimentation of some cocoa particles. Samples B and C were found to provide excellent stability with no signs of sedimentation and no visual signs of gelation. The additional tests that were performed as set forth in Table 2 showed no defects for samples A-C. As a result, the stabilizers of the present invention tested in this Example were unexpectedly found to be superior to the high performing commercial product.

Example 20

UHT Soy Beverage

Materials and Methods:

Samples of UHT soy beverages were prepared using A) commercial colloidal MCC/high DS, medium viscosity CMC from Example 16; B) colloidal MCC/high DS-low viscosity CMC as in Example 2 (inventive sample); C) colloidal MCC/mix of high DS-low viscosity CMC and low DS-low viscosity CMC as in Example 3 (inventive sample); D) colloidal MCC/mix of high DS-low viscosity CMC and low DS-low viscosity CMC as in Example 4 (inventive sample). The formulations are shown in Table 6.

TABLE 6

| Ingredients | Sample A % by wt | Sample B % by wt | Sample C % by wt | Sample D % by wt |
|---|---|---|---|---|
| Water | 89.47 | 89.47 | 89.47 | 89.47 |
| Sugar S2 | 6.12 | 6.12 | 6.12 | 6.12 |
| TCP C53-83 Buddenheim 3 microns | 0.33 | 0.33 | 0.33 | 0.33 |
| Tri-Sodium Citrate | 0.05 | 0.05 | 0.05 | 0.05 |
| Supro 760, Solae | 3.75 | 3.75 | 3.75 | 3.75 |

TABLE 6-continued

| Ingredients | Sample A % by wt | Sample B % by wt | Sample C % by wt | Sample D % by wt |
|---|---|---|---|---|
| Sample A | 0.28 | | | |
| Sample B | | 0.28 | | |
| Sample C | | | 0.28 | |
| Sample D | | | | 0.28 |
| Total | 100 | 100 | 100 | 100 |

Process:

Isolated soya protein, sodium citrate, and 600 g sugar were added to the water heated to 167° F. Materials were allowed to hydrate while mixing gently with a Silverson mixer to avoid foaming. A dry blend of the colloidal MCC stabilizer and 200 grams of sugar were added to the mixture and allowed to agitate for 5 minutes. The remaining sugar and TCP were then added and allowed to mix for an additional 5 minutes. The pH was checked and recorded. The product was then transferred to the Micro Thermics® UHT/HTST Direct & Indirect Processing System assembled to deliver the following temperature sequences and holding time. The unprocessed mixture was first preheated to 176° F. followed by immediate indirect steam sterilization in the final heater. Product was held at 284° F. for 6 seconds followed by cooling to 150° F. Two-stage homogenization was employed (2,500 first stage/500 psi $2^{nd}$ stage). The sterilized mix was further cooled to ~70° F. where the product was filled into ¼ litre clear nalgene bottles inside of a Clean-Fill Hood & Sterile Product Outlet. Bottles were stored at 4° C., 20° C., and 30° C. Beverages were analyzed for stability based on visual parameters and scale as described previously in Table 2 (Example 20).

Conclusion (two weeks observation): Samples B, C and D provided good functionality and very slight sediment (such sediment being very easy to re-disperse) and such results were comparable to the high performing commercial Sample A. The additional tests that were performed as set forth in Table 2 showed no defects for samples A-D.

Example 21

UHT Soy Beverage

Materials and Methods:

Samples of UHT soy beverages were prepared using A) commercial colloidal MCC/high DS, medium viscosity CMC as described in Example 16 (control); B) colloidal MCC/mix of high DS-low viscosity CMC and low DS-medium viscosity CMC as in Example 6 (inventive sample); C) pilot-scale colloidal MCC/mix of high DS-low viscosity CMC and low DS-medium viscosity CMC as in Example 7 (inventive sample). The formulations are shown in Table 7.

TABLE 7

| Ingredients | Sample A % by wt | Sample B % by wt | Sample C % by wt |
|---|---|---|---|
| Water | 89.47 | 89.55 | 89.50 |
| Sugar S2 | 6.12 | 6.12 | 6.12 |
| TCP C53-83 Buddenheim 3 microns | 0.33 | 0.33 | 0.33 |
| Tri-Sodium Citrate | 0.05 | 0.05 | 0.05 |
| Supro 760, Solae | 3.75 | 3.75 | 3.75 |

TABLE 7-continued

| Ingredients | Sample A % by wt | Sample B % by wt | Sample C % by wt |
|---|---|---|---|
| Sample A | 0.28 | | |
| Sample B | | 0.20 | |
| Sample C | | | 0.25 |
| Total | 100 | 100 | 100 |

Process:

Isolated soya protein, sodium citrate, and 300 g sugar were added to the water heated to 75° C. Materials were allowed to hydrate while mixing gently with a Silverson mixer to avoid foaming. A dry blend of the colloidal MCC stabilizer and 40 grams of sugar was added while mixing. Then the remaining sugar and TCP were added and allowed to mix. The pH was checked to ensure ~pH 7. The product was then transferred to the UHT Processing System (Plate heat exchanger SPX) assembled to deliver the following temperature sequences and holding time. The unprocessed mixture was first preheated to 80° C., followed by upstream homogenization at 200 bar (150 first stage/50 second stage). The mix was heated at 140° C. for 5 seconds followed by cooling to 10° C. The sterilized product was filled aseptically into 250 ml clear Nalgene bottles. Bottles were stored at 4° C. Beverages were analyzed for viscosity, pH and stability based on visual parameters and scale as described previously in Table 2.

Conclusion (one day observation): All samples suspended the calcium perfectly. No defects were observed. Samples B and C displayed higher viscosities even at significantly lower dosages, indicating an unexpectedly better stabilization than the high performing commercial Sample A. The additional tests that were performed as set forth in Table 2 showed no defects for samples A-C.

While the invention has been described in detail and with reference to specific embodiments thereof, it will be apparent to one skilled in the art that various changes and modifications can be made therein without departing from the spirit and scope thereof.

What is claimed is:

1. A co-attrited stabilizer composition comprising:
   (i) microcrystalline cellulose,
   (ii) carboxymethyl cellulose, wherein said carboxymethyl cellulose has a degree of substitution of from 0.95 -1.5 and a viscosity of less than 50 cps, and
   (iii) at least one of a carboxymethyl cellulose having a degree of substitution of from 0.45 to 0.9 or a carboxymethyl cellulose having a DS of from 0.95 to 1.5 and a viscosity of 200 -4,000 cps.

2. The stabilizer composition of claim 1, wherein said viscosity is less than 25 cps.

3. The stabilizer composition of claim 1, wherein the microcrystalline cellulose is present in an amount of from 60-96% by total weight of the microcrystalline cellulose and carboxymethyl cellulose in said stabilizer composition, and said carboxymethyl cellulose of component (ii) is present in an amount of from 4 to 40% by total weight of the microcrystalline cellulose and carboxymethyl cellulose in said stabilizer composition.

4. The stabilizer composition of claim 1, wherein the carboxymethyl cellulose of component (iii) is present in an amount of from 2 to 36% by total weight of the stabilizer composition.

5. The stabilizer composition of claim 1, wherein said carboxymethyl cellulose of component (iii) having a DS of between 0.45 to 0.9 has a viscosity of 200 to 4,000 cps or a viscosity of 5 to 200 cps.

6. The stabilizer of claim 1, wherein said carboxymethyl cellulose of component (ii) has a degree of substitution of from 1.0-1.5.

7. The stabilizer of claim 1 consisting of said microcrystalline cellulose, said carboxymethyl cellulose of component (ii) and said carboxymethyl cellulose of component (iii).

8. The stabilizer of claim 1, wherein said stabilizer does not contain a starch.

9. A food comprising the stabilizer composition of claim 1.

10. The food of claim 9, wherein the food is a beverage.

11. The food of claim 10, wherein the beverage has a pH of from 2-7.

12. The food of claim 11, wherein the beverage comprises at least one of milk protein or plant protein.

13. The food of claim 12, wherein said plant protein comprises at least one soy protein or nut protein.

14. The food of claim 10, wherein the stabilizer composition is present in an amount of from 0.05 to 3.5% by total weight of the beverage.

15. An industrial composition comprising the stabilizer of claim 1, wherein said industrial composition is a pharmaceutical composition, veterinary composition, agricultural composition, or cosmetic composition.

16. A method of making the stabilizer composition of claim 1, comprising:
a) admixing the microcrystalline cellulose and carboxymethyl cellulose of components (ii) and (iii); b) co-attriting the admixture of step a); and c) drying the extrudent of step b).

* * * * *